US008136384B2

(12) United States Patent
Hannahs et al.

(10) Patent No.: US 8,136,384 B2
(45) Date of Patent: Mar. 20, 2012

(54) HARDBAND WEAR TESTING SYSTEM AND METHOD

(75) Inventors: Daniel L. Hannahs, Houston, TX (US); Irving O. Logan, Houston, TX (US); Alfred Calles, Jr., Houston, TX (US)

(73) Assignee: National Oilwell Varco, L.P., Houston, TX (US)

( * ) Notice: Subject to any disclaimer, the term of this patent is extended or adjusted under 35 U.S.C. 154(b) by 753 days.

(21) Appl. No.: 12/191,067

(22) Filed: Aug. 13, 2008

(65) Prior Publication Data

US 2010/0037675 A1 Feb. 18, 2010

(51) Int. Cl.
*G01N 3/56* (2006.01)
(52) U.S. Cl. .......................................... 73/7; 73/152.01
(58) Field of Classification Search ........... 73/7, 118.01, 73/152.01
See application file for complete search history.

(56) References Cited

U.S. PATENT DOCUMENTS

| | | | | |
|---|---|---|---|---|
| 3,800,891 | A | * | 4/1974 | White et al. ................... 175/374 |
| 4,224,382 | A | * | 9/1980 | Brown et al. ................. 428/656 |
| 4,243,727 | A | * | 1/1981 | Wisler et al. ................. 428/558 |
| 4,665,996 | A | * | 5/1987 | Foroulis et al. ................ 175/61 |
| 4,803,045 | A | * | 2/1989 | Ohriner et al. ................. 420/57 |
| 5,147,996 | A | * | 9/1992 | Carlin ........................ 219/76.14 |
| 5,633,094 | A | * | 5/1997 | Takeshima et al. ........... 428/679 |
| 5,667,903 | A | * | 9/1997 | Boyce .......................... 428/558 |
| 5,935,350 | A | * | 8/1999 | Raghu et al. .................. 148/427 |
| 6,124,564 | A | * | 9/2000 | Sue et al. ................. 219/121.47 |
| RE37,127 | E | * | 4/2001 | Schader et al. ................ 75/239 |
| 7,134,316 | B2 | * | 11/2006 | Kuhman et al. ...................... 73/7 |
| 2008/0283305 | A1 | * | 11/2008 | Overstreet et al. ............ 175/425 |

OTHER PUBLICATIONS

J.M. Schoenmakers, "Casing Wear During Drilling," JPT, Dec. 1987 SPE Drilling Engineering, pp. 375-381.
J.P. White and R. Dawson, "Casing Wear: Laboratory Measurements and Field Predictions,", Mar. 1987, SPE Drilling Engineering, pp. 56-62.
J. Steve Williamson, "Casing Wear: The Effect of Contact Pressure," JPT, Dec. 1981, Journal of Petroleum Technology, pp. 2382-2387.
C. Marx, H.J. Retelsdorf and P. Knauf, "Evaluation of New Tool Joint Hardfacing Material for Extended Connection Life," SPE/IADC, Amsterdam, Mar. 1991, pp. 871-875.
M.E. True and P.D Weiner, "Optimum Means of Protecting Casing and Drillpipe Tool Joints Against Wear," JPT, Feb. 1975, pp. 246-252.
F.J. Carlin, "What Really Wears Your Casing When New Hardmetals Are Used," Dallas, Feb. 1994, pp. 925-933, IADC/SPE 27533.
R.W. Hall, Jr., A. Garkasi, G. Deskins, J. Vozniak, Recent Advances in Casing Wear Technology, Dallas, Feb. 1994, IADC/SPE 27532, pp. 1-8.
Alvaro Chan, Dan Hannahs, Michael Jellison, Michael Brietsameter, Daniel J. Branagan, Harvey Stone, Greg Jeffers, "Evolution of Drilling Programs . . . " IADC/SPE 112740, Orlando, presented Mar. 2008, pp. 1-17. Alvaro Chan, Dan Hannahs, Scott Waters, "Evolution of Innovative Test Methodology . . . ", IADC/SPE 115206, Jakarta, Aug. 2008, pp. 1-15.

\* cited by examiner

*Primary Examiner* — Thomas P Noland
(74) *Attorney, Agent, or Firm* — Victor H. Segura

(57) ABSTRACT

A hardband wear testing system with a first rotatable member connected to a tool joint to rotate the tool joint in a first direction. A second rotatable member connectable to the casing sample to rotate the casing sample in the first direction or in a second direction opposite to the first direction. One or more actuators may be utilized to raise and lower the second rotatable member and the casing sample with respect to the tool joint.

24 Claims, 4 Drawing Sheets

HARDBAND WEAR TESTING SYSTEM AND METHOD

BACKGROUND

1. Technical Field

The present invention relates generally to the field of tool joints and casing and, more specifically, to systems and methods for testing and/or calculating and/or projecting wear related to hardbands.

2. Description of Related Art

Drilling strings and casing strings are a large expense of subsurface drilling operations. Hardbands, also known as tool joint hardfacing, have been utilized for decades to prolong tool joint life of drill pipe by reducing outside diameter wear while simultaneously attempting to minimize wear to the inside diameter of the casing. Hardbands typically do not cover the entire length of the tool joint and may often be only about three inches or so in length.

In order to evaluate different types of hardbands and/or casing, wear producing machines are utilized to simulate downhole wear. For example, downhole wear may occur due to contact between the hardband and the inside of casing.

Machines to test hardband wear, some of which are discussed below, provide means for rotating the tool joint against a casing sample. Such machines have been in use for several decades. A measured contact load is applied between the tool joint and the casing sample. The casing sample is typically axially reciprocated while the tool joint is rotated. A fluid, such as one of various types of drilling fluids, may be circulated over the contact region between the tool joint and the casing. Various means for determining the wear are utilized, and the results may be applied to a graph for comparison and evaluation.

The present inventors have found that prior art wear machines to test hardbands over the last several decades tend to produce results that are not sufficiently accurate with respect to repeatability. The inventors herein disclose solutions that have improved repeatability of hardband wear tests up to 300%.

The following references describe the above and other related material:

The article entitled "Optimum Means of Protecting Casing and Drillpipe Tool Joints Against Wear," by M. E. True and P. D. Weiner, printed in February 1975 in the *Journal of Petroleum Technology*, describes the results of 267 tool-joint tests and other related tests made under various conditions such as tests carried out in water, in two weights of water muds, and in oil-based muds. A machine is disclosed for carrying out the tests.

The article entitled "Casing Wear: The Effect of Contact Pressure," by J. Steve Williamson, printed in December 1981 in the *Journal of Petroleum Technology*, describes a new test machine and experimental procedure used to study the effect of contact loads on casing wear. A machine is disclosed for carrying out the tests.

The article entitled "Casing Wear During Drilling: Simulation, Prediction, and Control" by J. M. Schoenmakers, printed in December 1987 in the *Journal of Petroleum Technology*, describes four case studies that show laboratory simulations of casing wear caused by rotating tool joint hardfacings correspond very well to field-measured casing wear. A machine is disclosed for carrying out the tests.

The article entitled "Casing Wear: Laboratory Measurements and Field Predictions" by J. P. White and R. Dawson, printed in March 1987 in the *Journal of Petroleum Technology*, describes an experimental program devised to measure casing wear in a full-scale test machine. A machine is disclosed for carrying out the tests.

The article entitled "Evaluation of New Tool Joint Hardfacing Material for Extended Connection Life and Minimum Casing Wear" by C. Marx, H. J. Retelsdorf, and P. Knauf, printed in March 1991 for presentation at the 1991 SPE/IADC Drilling Conference held in Amsterdam, describes a new testing facility allowing a combination of axial movement and rotation.

The article entitled "Recent Advances in Casing Wear Technology" by R. W. Hall, Jr., A. Garkasi, G. Deskins, and J. Vozniak, printed in February 1994 for presentation at the 1994 SPE/IADC Drilling Conference held in Dallas, Tex., provides a mathematical description of the casing wear process and an experimental determination of the wear factors which are an integral part of the casing wear model. The figures show a cross-section of a crescent-shaped wear groove in casing due to tool joint contact.

The article entitled "What Really Wears Your Casing When New Hardmetals Are Used" by F. J. Carlin, printed in February 1994 for presentation at the 1994 SPE/IADC Drilling Conference held in Dallas, Tex., discusses test results that indicate when new hardfacing materials are used that casing wear is dramatically reduced. A test machine is discussed.

While the above publications address many factors regarding the wear of drill strings and casing, the problem of repeatability of hardband wear tests remains to be addressed. Consequently, there remains a long felt need for improved equipment and methods, which significant reduce repeatability errors. Those skilled in the art have long sought and will appreciate the present invention, which addresses these and other problems.

SUMMARY

Aspects of the invention provide improved techniques for simulating wear involving a hardband on a tool joint, and for comparing wear rates for different types of hardbands.

One aspect of the invention provides a method for hardband wear testing between a hardband of a tool joint and a casing sample. The method includes securing the tool joint to a first rotatable member; securing the casing sample to a second rotatable member; rotating the first rotatable member with a first rotary drive; rotating the second rotatable member with a second rotor drive; positioning the tool joint within the casing sample; and moving the second rotatable member and the casing sample with respect to the tool joint and the first rotatable member.

Another aspect of the invention provides a method for hardband wear testing between a hardband of a tool joint and a casing sample. The method includes rotating the tool joint in a first direction; rotating the casing sample in a second direction opposite to the first direction; and frictionally engaging the tool joint and the casing sample.

Another aspect of the invention provides a method for hardband wear testing between a hardband of a tool joint and a casing sample. The method includes connecting the casing sample to a holder; supporting the holder utilizing a plurality of cylindrical rollers; and moving the plurality of cylindrical rollers to engage the tool joint with the casing sample.

Another aspect of the invention provides a hardband wear testing system to test wear between a hardband of a tool joint and a casing sample. The system includes a holder adapted to receive the casing sample; a housing surrounding the holder; a plurality of vertical guide assemblies secured to opposite sides of the housing, the plurality of vertical guide assemblies being adapted to permit vertical movement of the housing and prevent horizontal and axial movement of the housing; and at least one actuator connectively secured to the housing operable to raise and lower the casing sample with respect to the tool joint.

Another aspect of the invention provides a method for hardband wear testing between a hardband of a tool joint and a casing sample. The method includes connecting the casing sample to a holder; supporting the holder within a housing; mounting a plurality of vertical guide assemblies to opposite sides of the housing, the plurality of vertical guide assemblies being adapted to permit vertical movement of the housing and prevent horizontal and axial movement of the housing; and engaging the casing sample with the tool joint.

BRIEF DESCRIPTION OF THE DRAWINGS

The drawings depict aspects of the invention embodied in various forms. It is to be understood that in some instances various aspects of the invention may be shown exaggerated or enlarged with certain features emphasized to facilitate an understanding of the invention. The drawings are not intended to limit the claims to the invention in any way but instead show particular or possible embodiments that are believed to be useful to those of skill in the art to illustrate underlying concepts of the invention.

DETAILED DESCRIPTION

Figure 1:
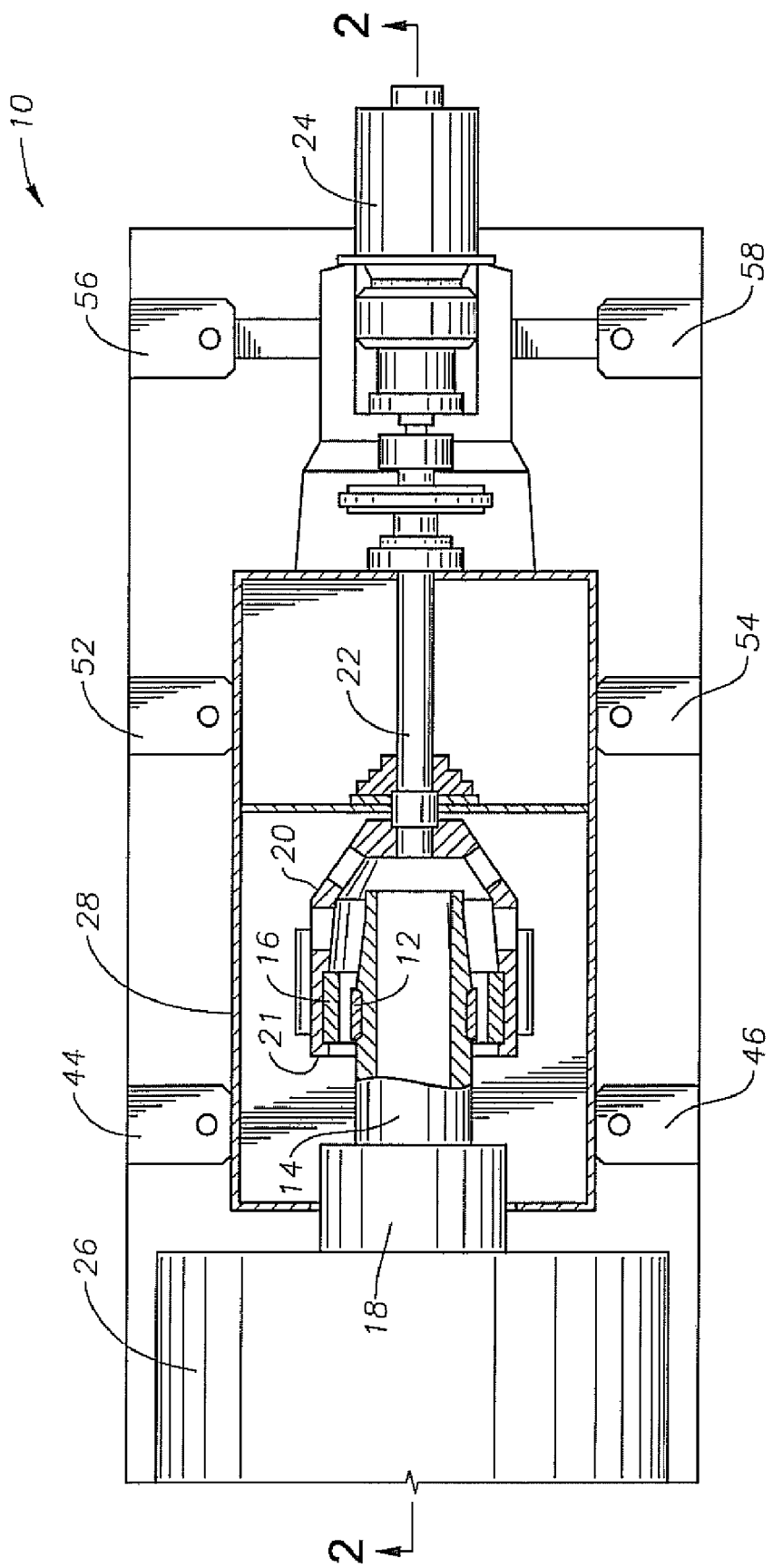
FIG. 1 is a plan view, partially in section, illustrating a hardband test system and method in accord with an aspect of the invention.
Figure 2:
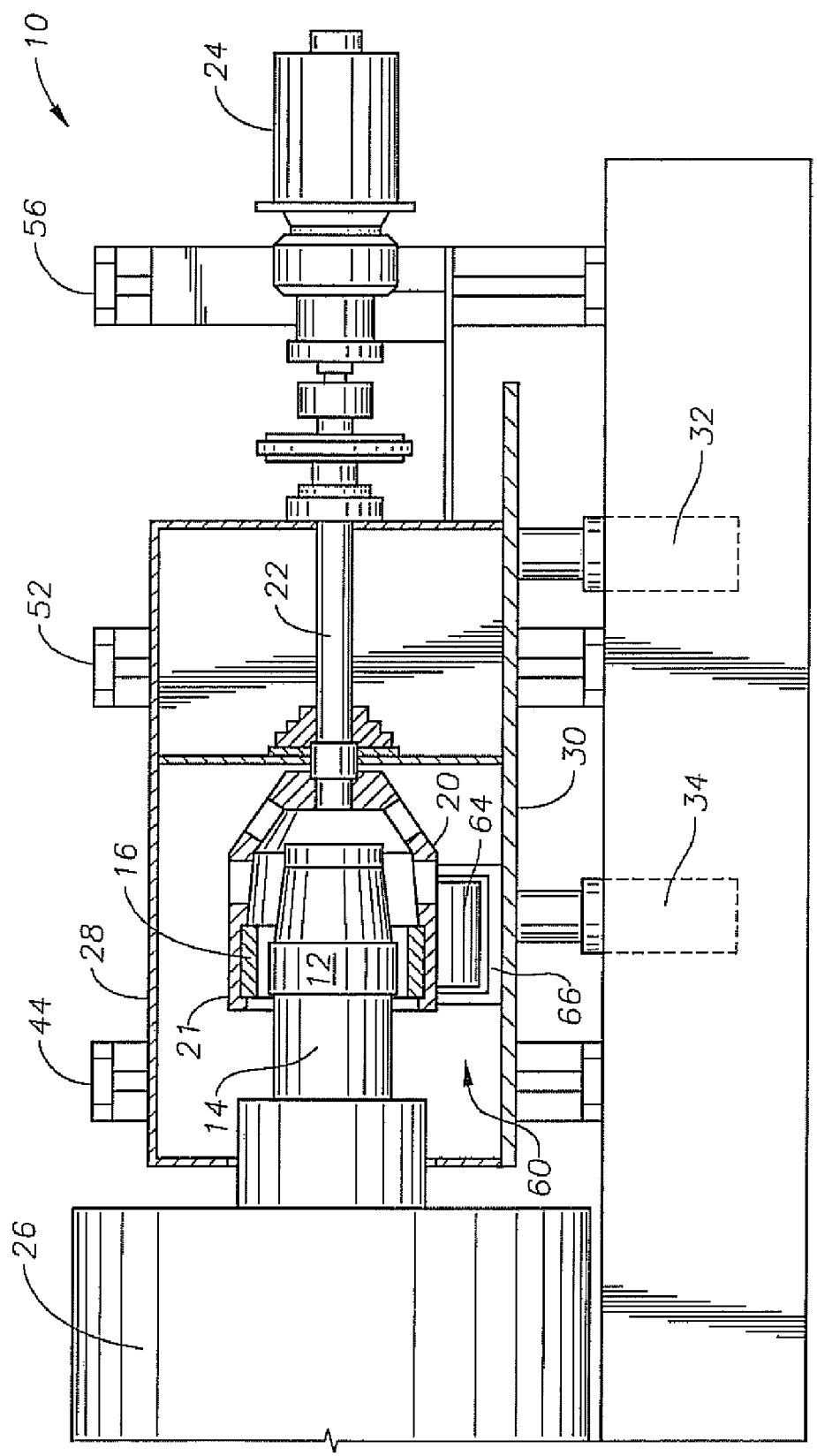
FIG. 2 is an elevational view, partially in section, illustrating the hardband test system of FIG. 1 at a cross-section taken along line 2-2 of FIG. 1 prior to applying pressure to a test piece in accord with an aspect of the invention.
Figure 3:
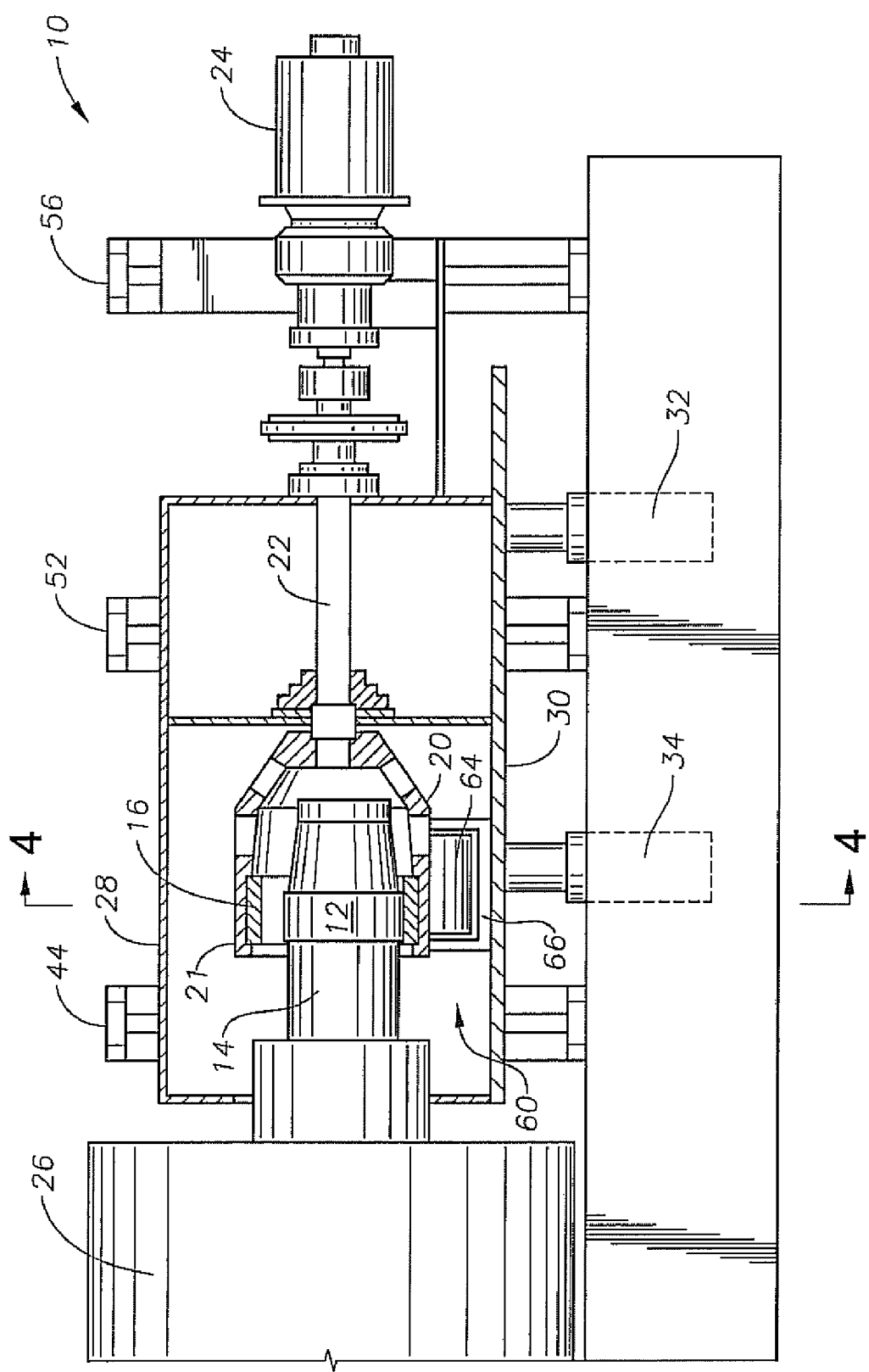
FIG. 3 is an elevational view, partially in section, illustrating the hardband test system of FIG. 1 at a cross-section taken along line 2-2 of FIG. 1 while applying pressure to a test piece in accord with an aspect of the invention.

Referring to the drawings, hardband wear machine 10 may be utilized to test hardband 12 of tool joint 14 for wear in casing sample 16, as shown in FIGS. 1, 2, 3, and 4. As best shown in FIGS. 1-3, tool joint 14 is mounted into primary spindle 18. Casing sample 16 is mounted in holder 20. Casing sample 16 may be comprised of L-80 metal material or any material grade as desired. End piece or retainer ring 21 may be bolted or otherwise secured to the end of holder 20 to secure casing sample 16 within holder 20. Holder 20 may be rotated utilizing secondary spindle 22 and corresponding secondary motor 24. Primary spindle 18 may be rotated utilizing primary motor 26. Accordingly, in one aspect, the invention provides first and second rotary drives, which may be selectively utilized to independently rotate casing sample 16 and tool joint 14 and other rotatable members at different speeds and in the same or different directions as desired.

Housing 28 may be utilized to enclose tool joint 14 and casing sample 16 during testing. Drilling fluid (not shown) or other fluids may be injected and/or sprayed and/or contained and/or circulated through housing 28 during testing.

Figure 4:
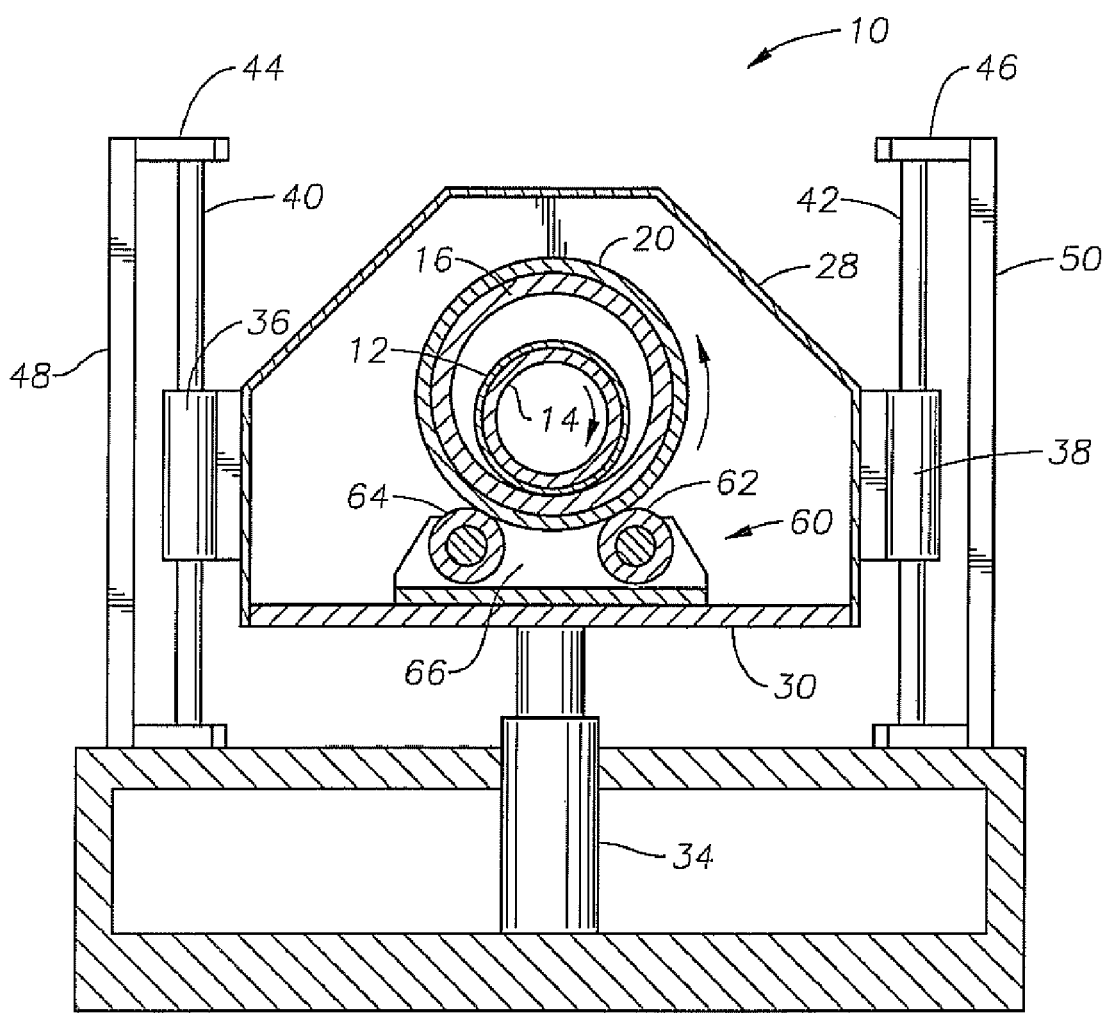
FIG. 4 is an elevational view, partially in section, illustrating the hardband test system of FIG. 3 at a cross-section taken along line 4-4 of FIG. 3 while applying pressure to a test piece in accord with an aspect of the invention.

Referring to FIGS. 2-4, floating table 30 provides a floor or support for housing 28. Hydraulic or pneumatic actuators such as hydraulic or pneumatic actuators 32 and 34 may be utilized to raise and lower floating table 30. Referring to FIG. 4, guide assemblies 44 and 46 may be utilized to insure that housing 28 is limited or constrained to vertical movement. In this aspect, guides 36 and 38 move up and down alignment shafts 40 and 42. Alignment shafts 40 and 42 are further supported by mounting brackets 48 and 50.

As shown in FIG. 1, additional guide assemblies such as guide assemblies 52, 54, 56 and 58 may be utilized to ensure that the entire assembly of floating table 30, housing 28, motor 24, spindle 22, and holder 20 are constrained to move vertically with horizontal and axial movement being prevented or significantly limited. Thus, movement of these components is highly controlled.

Referring to FIG. 4, there is shown holder 20 supported by roller assembly 60. Roller assembly 60 may comprise a plurality of rollers such as, in this example, roller 62 and roller 64 mounted in frame 66. In one aspect, rollers 62 and 64 are cylindrical. Roller assembly 60 is supported by floating table 30 and is utilized to apply a desired amount of force to holder 20. Roller assembly 66 is centralized so that both rollers 62 and 64 are evenly spaced from the center of holder 20. In this way, movement of floating table 30 provides a combined force from symmetrically positioned rollers 62 and 64 to provide a force on holder 20 that is directed vertically. Roller 62 and 64 also act to limit or prevent side-to-side movement of holder 20. Cylindrically shaped rollers also provide significant frictional force against axial movement.

In one aspect of the invention, hydraulic or pneumatic actuators 32 and 34 comprise electronic sensors to measure the amount of force produced. Electronic torque sensors may be utilized in conjunction with primary spindle 18 and secondary spindle 22. Rotational speed sensors may also be associated with primary spindle 18 and secondary spindle 22. This information and other information may be supplied to a computer via electronic connections and displayed or changed or controlled during testing.

Prior to testing, tool joint 14 and casing sample 16 are cleaned and then carefully measured by various means such as weighing and dimension checking with OD micrometers, ID micrometers, ultrasonic thickness meter, and the like. The same measurements may be repeated at desired intervals during testing. Other measurement such as measuring the linear length of hardband 12 may be made. Various markings may be made on these pieces as desired which may aid the operator in determining wear patterns.

Casing sample 16 may then be mounted to holder 22 and end piece or retainer ring 21 may be used to secure casing sample 16 into position. Tool joint 14 may be mounted to primary spindle 18. A check may be made to verify that casing sample 16 and tool joint 14 are axially aligned. Valves may be opened to permit flow of the drilling fluid or the like.

Primary spindle 18 and secondary spindle 22 may be started turning such as by adjusting variable frequency drives (VFD's), either manually or under computer control, to obtain the correct rotational speeds. Referring to FIG. 4, secondary spindle 22 and holder 20 may be rotated counter-clockwise. Primary spindle 18 and tool joint 14 may be rotated in the opposite direction, or clockwise. In one aspect, secondary spindle 22 and holder 20 are rotated at 4 rpm and primary spindle 18 and tool joint 14 are rotated in the opposite direction at 156-158 rpm. A possible range of speed for primary spindle 18 may typically be 155-165 rpm. A broader range of speed may be from 125-185 rpm, although a suitable desired speed within or outside of this range may be selected to simulate operational wear. A possible range of speed for its secondary spindle 22 may be from 2-10 rpm.

In FIG. 2, tool joint 14 and hardband 12 may be centralized within casing sample 16 and holder 20. It will be recalled that holder 20 rests on roller assembly 60. In FIG. 3, hydraulic or pneumatic actuators 32 and 34 may be activated to raise floating table 30, roller assembly 60 and holder 20. Motor 24 may be supported to move vertically with floating table 30 so that the entire drive assembly for rotating holder 20 moves together. In one example, the desired force applied by hydraulic or pneumatic actuators 32 and 34 is set to 250 pounds per linear inch of hardband 12.

It has been found that wear tests repeat with much greater accuracy than was available in the prior art. Whereas prior art machines normally utilize axial movement during wear tests, axial movement according to the present invention is preferably prevented. Moreover, both hardband 12 and casing sample 16 may be rotated in opposite directions. It is believed that in prior art machines, due to creation of a groove during testing, the engagement surface area changes significantly during the wear test. Accordingly, the wear pattern itself may affect the results. As well, the method of applying force in prior art machines, often by hinged a mechanism or the like, does not result in the force being directed purely vertically in a repeatable manner. As well, all electronic sensors and/or computer controls provide measurements that are more accurate.

Due to the various changes made in accord with aspects of the present invention discussed herein, a reduction of repeatability errors of up to 300% have been found.

It will be apparent to those skilled in the art that aspects of the invention may be implemented using one or more suitable general-purpose computers having appropriate hardware and programmed to perform the techniques disclosed herein. The programming may be accomplished through the use of one or more program storage devices readable by the computer processor and encoding one or more programs of instructions executable by the computer for performing the operations described above. The program storage device may take the form of, e.g., one or more floppy disks; a CD ROM or other optical disk; a magnetic tape; a read-only memory chip (ROM); and other forms of the kind well known in the art or subsequently developed. The program of instructions may be "object code," i.e., in binary form that is executable more-or-less directly by the computer; in "source code" that requires compilation or interpretation before execution; or in some intermediate form such as partially compiled code. The precise forms of the program storage device and of the encoding of instructions are immaterial here. Aspects of the invention may also be implemented using conventional display means situated as desired to display the processed or raw data/images as known in the art.

While the present disclosure describes specific aspects of the invention, numerous modifications and variations will become apparent to those skilled in the art after studying the disclosure, including use of equivalent functional and/or structural substitutes for elements described herein. All such similar variations apparent to those skilled in the art are deemed to be within the scope of the invention as defined by the appended claims.

What is claimed is:

1. A hardband wear testing system to test wear between a hardband of a tool joint and a casing sample, comprising:
    a holder adapted to receive said casing sample;
    a housing surrounding said holder;
    a plurality of vertical guide assemblies secured to opposite sides of said housing, said plurality of vertical guide assemblies being adapted to permit vertical movement of said housing and prevent horizontal and axial movement of said housing; and
    at least one actuator connectively secured to said housing operable to raise and lower said casing sample with respect to said tool joint.

2. The hardband wear testing system of claim 1 comprising a plurality of cylindrical rollers mounted within said housing to support said holder.

3. The hardband wear testing system of claim 1 comprising a first rotatable member connected to said tool joint to rotate said tool joint in a first direction, and a second rotatable member connected to said holder to rotate said holder in a second direction opposite to said first direction.

4. The hardband wear testing system of claim 3 wherein said at least one actuator is interconnected with said housing and said second rotatable member whereby said at least one actuator is operable to raise and lower said housing and said second rotatable member with respect to said first rotatable member and said tool joint.

5. The hardband wear testing system of claim 3 comprising a first rotary drive configured to rotate said first rotatable member at a speed of 125 rpm to 185 rpm.

6. The hardband wear testing system of claim 5 comprising a second rotary drive configured to rotate said second rotatable member at a speed of 2 rpm to 10 rpm.

7. The hardband wear testing system of claim 1 comprising a first rotatable member connected to said tool joint to rotate said tool joint in a first direction, and a second rotatable member connected to said holder to rotate said holder in said first direction.

8. The hardband wear testing system of claim 1 wherein:
    said tool joint is securable to a first rotatable member;
    said casing sample is securable to a second rotatable member;
    wherein said first rotatable member is rotatatable with respect to a first rotary drive and said second rotatable member is rotatable with a second rotary drive;
    wherein said tool joint is positionable within said casing sample; and
    wherein said second rotatable member and said casing sample is moveable with respect to said first rotatable member and said tool joint.

9. The hardband wear testing system of claim 8 wherein said first rotatable member is rotatable in a first direction, and said second rotatable member is rotatable in a second direction opposite to said first direction.

10. The hardband wear testing system of claim 8 wherein said first rotatable member and said second rotatable member are rotatable in the same direction.

11. The hardband wear testing system of claim 8 wherein said first rotatable member is rotatable at a speed between 125 rpm and 185 rpm.

12. The hardband wear system of claim 8 wherein said second rotatable member is rotatable at a speed between 2 rpm and 10 rpm.

13. The hardband wear testing system of claim 8 wherein said casing sample is connectable to said holder, and said holder is supportable by utilizing a plurality of cylindrical rollers.

14. The hardband wear testing system of claim 1 wherein:
    said tool joint is rotatable in a first direction and said casing sample is rotatable in a second direction opposite to said first direction; and
    wherein said tool joint and said casing sample are frictionally engagable.

15. The hardband wear testing system of claim 14 wherein said tool joint is rotatable at a speed between 125 rpm and 185 rpm.

16. The hardband wear testing system of claim 15 wherein said casing sample is rotatable at a speed between 2 rpm and 10 rpm.

17. The hardband wear testing system of claim 14 wherein said casing sample is connectable to said holder and said holder is supportable utilizing a plurality of cylindrical rollers.

18. The hardband wear testing system of claim 14 wherein said casing sample is connectable to said holder, said holder is supportable within said housing, and said plurality of vertical guide assemblies are mountable to opposite sides of said housing.

19. The hardband wear testing system of claim 1 wherein said casing sample is connectable to said holder, said holder supportable by a plurality of cylindrical rollers, and said plurality of cylindrical rollers movable to engage said tool joint with said casing sample.

20. The hardband wear testing system of claim 19 wherein said tool joint is rotatable in a first direction, and said holder is rotatable in a second direction opposite to said first direction.

21. The hardband wear testing system of claim 19 wherein said tool joint and said holder are rotatable in the same direction.

22. The hardband wear testing system of claim 19 wherein said tool joint is rotatable utilizing a first rotatable member, said holder is rotatable utilizing a second rotatable member, and said plurality of cylindrical rollers and a second rotatable member are movable vertically to engage said tool joint with said casing sample.

23. The hardband wear testing system of claim 19 wherein a rotatable member is rotatable at a speed between 125 rpm and 185 rpm.

24. The hardband wear testing system of claim 23 wherein a second rotatable member is rotatable at a speed between 2 rpm and 10 rpm.

* * * * *